United States Patent [19]
Breidenthal et al.

[11] Patent Number: 6,139,490
[45] Date of Patent: *Oct. 31, 2000

[54] STEREOSCOPIC ENDOSCOPE WITH VIRTUAL REALITY VIEWING

[75] Inventors: Robert S. Breidenthal, Bolton; Richard E. Forkey, Westminster; Jack Smith, Sudbury; Brian E. Volk, Jefferson, all of Mass.

[73] Assignee: Precision Optics Corporation, Gardner, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/966,827

[22] Filed: Nov. 10, 1997

Related U.S. Application Data

[63] Continuation-in-part of application No. 08/883,216, Jun. 26, 1997, Pat. No. 5,980,453, which is a continuation-in-part of application No. 08/605,593, Feb. 22, 1996, abandoned.

[51] Int. Cl.$^7$ ..................................................... A61B 1/04
[52] U.S. Cl. .............................. 600/111; 600/166; 348/45
[58] Field of Search .................................. 600/111, 166, 600/109; 348/45; 359/434

[56] References Cited

U.S. PATENT DOCUMENTS

| | | |
|---|---|---|
| 3,067,648 | 12/1962 | Cohen . |
| 3,520,587 | 7/1970 | Tasaki et al. .............................. 350/36 |
| 3,901,220 | 8/1975 | Koyasu et al. ............................... 128/6 |
| 4,061,135 | 12/1977 | Widran et al. . |
| 4,111,529 | 9/1978 | Yamashita ................................ 350/225 |
| 4,395,731 | 7/1983 | Schoolman . |
| 4,559,555 | 12/1985 | Schoolman . |
| 4,623,223 | 11/1986 | Kempf .................................... 350/138 |
| 4,651,201 | 3/1987 | Schoolman . |
| 4,827,909 | 5/1989 | Kato et al. . |
| 4,836,188 | 6/1989 | Berry . |
| 4,838,247 | 6/1989 | Forkner ....................................... 128/6 |
| 4,862,873 | 9/1989 | Yajima et al. . |
| 4,924,853 | 5/1990 | Jones, Jr. et al. . |
| 4,926,257 | 5/1990 | Miyazaki ................................ 358/98 |
| 5,122,650 | 6/1992 | McKinley . |
| 5,191,203 | 3/1993 | McKinley . |
| 5,222,477 | 6/1993 | Lia et al. . |
| 5,261,404 | 11/1993 | Mick et al. . |
| 5,305,121 | 4/1994 | Moll ........................................... 348/45 |
| 5,327,283 | 7/1994 | Zobel ..................................... 359/434 |
| 5,385,138 | 1/1995 | Berry ......................................... 128/6 |
| 5,400,177 | 3/1995 | Petitto et al. ........................... 359/451 |
| 5,417,210 | 5/1995 | Funda et al. ......................... 128/653.1 |
| 5,424,877 | 6/1995 | Tsuyuki et al. ......................... 359/663 |
| 5,459,605 | 10/1995 | Kempf ................................... 359/462 |
| 5,474,519 | 12/1995 | Bloomer .................................. 600/111 |
| 5,488,952 | 2/1996 | Schoolman ......................... 178/660.07 |
| 5,527,263 | 6/1996 | Zobel et al. ............................. 600/166 |
| 5,577,991 | 11/1996 | Akui et al. ............................... 600/111 |
| 5,588,949 | 12/1996 | Taylor et al. ........................... 600/166 |
| 5,603,687 | 2/1997 | Hori et al. ............................... 600/166 |
| 5,647,838 | 7/1997 | Bloomer .................................. 600/111 |
| 5,702,350 | 12/1997 | Vry et al. ................................. 600/166 |

*Primary Examiner*—John P. Leubecker
*Attorney, Agent, or Firm*—Pearson & Pearson

[57] ABSTRACT

A stereoscopic endoscope system for producing images that can be perceived in three dimensions. An endoscope apparatus includes a sheath carrying a light source and two independent fixed lens endoscopes. Collimated light from the proximal ends of each endoscope are directed along folded optical paths to independent video cameras. The images generated by the video cameras energize monitors in a virtual reality display device that can be positioned proximate an observer's eyes. Adjustable mirrors and the provision of the rotation of at least one of the video cameras on its axis facilitate the alignment of the images for maximum effect.

19 Claims, 6 Drawing Sheets

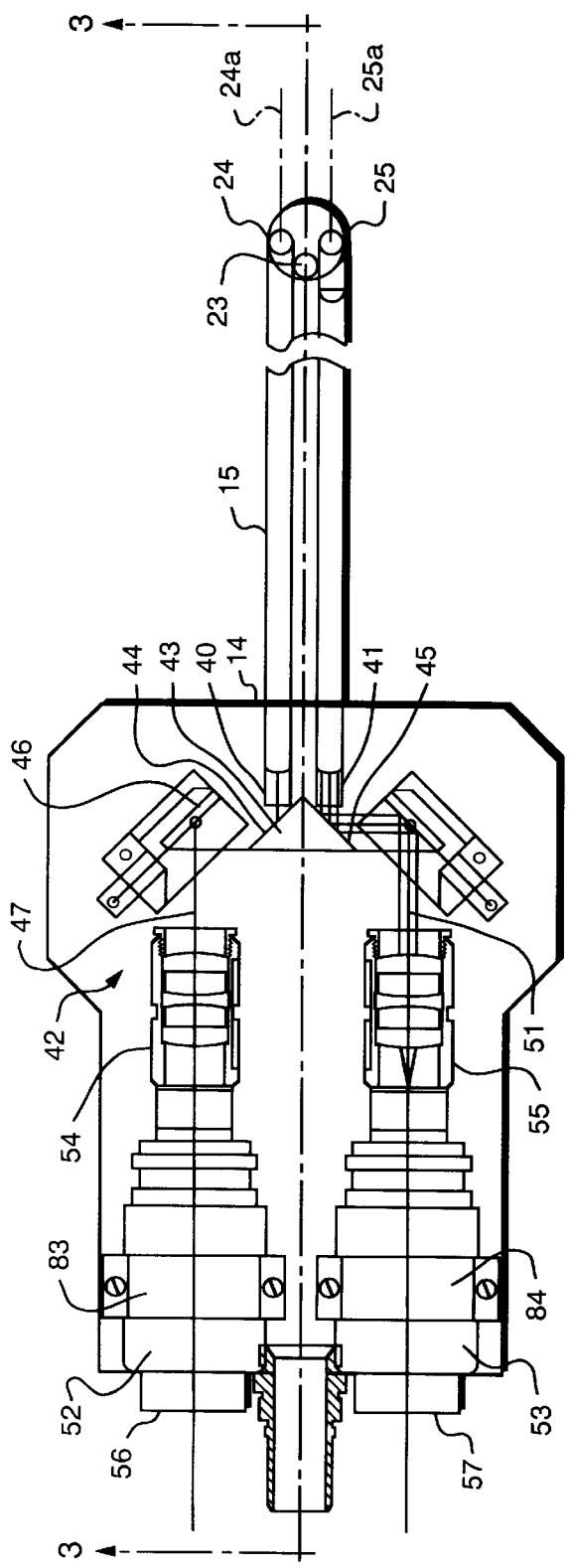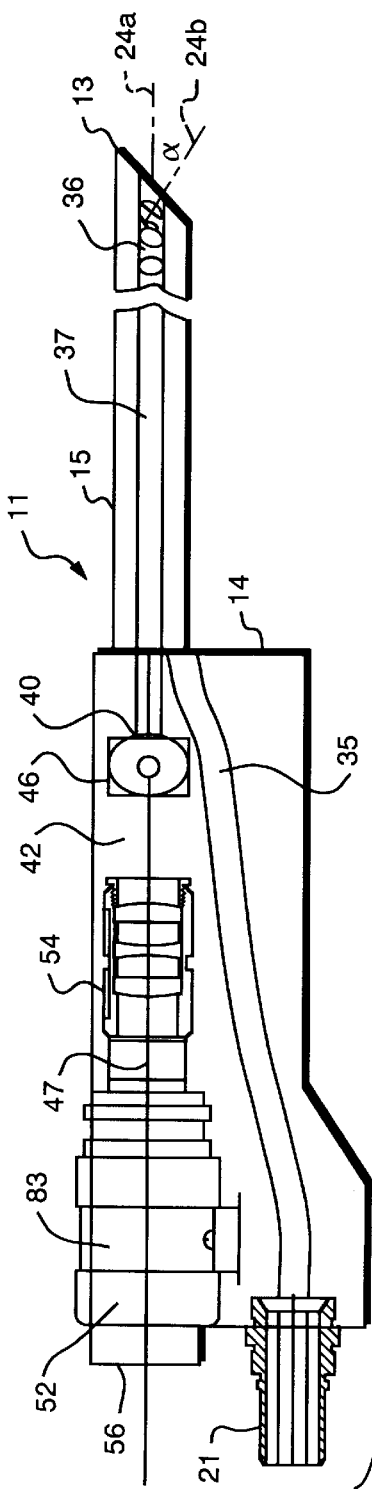

STEREOSCOPIC ENDOSCOPE WITH VIRTUAL REALITY VIEWING

CROSS-REFERENCE TO RELATED APPLICATION

This application is a continuation-in-part of patent application Ser. No. 08/883,216 filed Jun. 26, 1997, now U.S. Pat. No. 5,980,453, titled Endoscope with Low Distortion and assigned to the same assignee as this invention which is a continuation-in-part of Ser. No. 08/605,593 filed Feb. 22, 1996 (now abandoned).

BACKGROUND OF THE INVENTION

1. Field of the Invention

This invention relates generally to viewing scopes and more particularly to an endoscope that facilitates three-dimensional viewing.

2. Description of Related Art

Endoscopes have attained great acceptance within the medical community in connection with a number of procedures. This acceptance exists because endoscopes provide a means for performing procedures with minimal patient trauma while enabling a physician to view directly the internal anatomy of a patient. Over the years a number of endoscopes have been developed and have been categorized according to specific applications. Many have specific names including arthroscopes, cystoscopes, proctoscopes, laparoscopes and laryngoscopes. Industrial endoscopes are often called borescopes.

In whatever specific form, an endoscope generally comprises an objective lens system at the distal end of the endoscope that forms an image of an object. With medical endoscopes the object generally is within a patient in some environmental media such as air, water, a saline solution or the like. Industrial endoscopes image objects that may be located in a remote enclosed volume. An eyepiece or ocular system at the proximal end presents the image for viewing visually, electronically or otherwise externally of the patient or enclosed volume. An image transfer system intermediate the objective and the eyepiece systems transfers the image produced by the objective lens system to the eyepiece system.

Significant efforts have been undertaken to improve the optical designs of these endoscopes with attention at various times directed to individual ones of the constituent optical systems. The above-identified application Ser. No. 08/883, 216 describes one system with an objective lens that facilitates the design of endoscopes that produce images with low distortion. Other efforts have been directed to improving the display of such an image.

Typically endoscopic displays are monoscopic or two-dimensional that, as known, do not facilitate depth perception. Yet in many modalities depth perception would be advantageous if available. For example, a three-dimensional view would simplify a surgeon's task in bringing two implements of identical shape but different sizes together in predictable and repeatable manner. It is very difficult to achieve that feat with a two-dimensional image.

The efforts in developing displays to improve depth perception have taken different approaches. In accordance with one approach, direct viewing devices produce stereoscopic images. For example, in U.S. Pat. No. 3,520,587 to Tasaki et al. two elongated flexible optical fiber systems with independent objective lenses focus images to be inspected. The images are then transmitted to a proximal end through light bundles that are incident to the respective objective lens systems to form a parallax angle that creates a visual perception of a three-dimensional object.

U.S. Pat. No. 4,061,135 to Widran et al. discloses a binocular endoscope in which a non-distorting, high resolution, optical system utilizing long path length lenses conveys the image of a viewed object onto two optical paths. Prisms and other optical elements provide folded optical paths to two lenses in binocular eye pieces to produce an image with depth perception.

U.S. Pat. No. 4,386,602 to Sheldon et al. discloses an intracranial surgical operative apparatus. A pair of endoscopes extend along converging endoscope axes. When a surgeon views an object through the two eyepieces, the surgeon perceives a stereoscopic or three-dimensional image.

U.S. Pat. No. 4,836,188 to Berry discloses an instrument for providing stereoscopic viewing of a body cavity. A head mounted unit includes optical elements in a folded optical path that convey an image to eyepieces. Light reflected from the object is split into two beams that are directed through the eyepieces to the eyes of the viewing surgeon.

U.S. Pat. No. 4,834,518 to Barber discloses another instrument for enabling a surgeon to visualize a three-dimensional image. This instrument uses fiber optics to convey images to left and right proximal lens systems disposed in eyepieces from distal left and right objective lens systems. The distal objective lens systems have converging optical axes to enable depth perception of an object.

In accordance with another development approach, a pair of images are displayed on a television monitor screen so a surgeon can "fuse" the images into a single image with perceived depth. For example, in U.S. Pat. No. 4,429,328 to Jones, Jr. et al. apparatus produces a three-dimensional illusion through the sequential display of images viewed alternatively from different points of origin at a rate which allows the eye to fuse the image. The maximum effect is achieved when the points of origin are vertically aligned with respect to one another and displaced from one another by a distance less than the normal interocular distance.

U.S. Pat. No. 4,528,587 to Jones, Jr. discloses apparatus in which first and second video cameras view an object from different points of origin. A switching device alternately couples frames from the two video cameras to produce a composite picture on a viewing device, such as a television set. The individual who views the image relies on image fusion to produce an image with perceived depth.

U.S. Pat. No. 4,656,508 to Yokota discloses an endoscope in which light produces a lattice-shaped light pattern on the object. An objective lens system directs the images to an image sensor that produces electrical signals to produce an image. A control synchronizes with the operation of the illumination light supply to process the resulting image with a three-dimensional effect.

U.S. Pat. No. 4,862,873 to Yajima et al. discloses apparatus with first and second optical guides. During alternate operating intervals light is transmitted through one optical guide with the reflected image being transferred to the other. During the next interval the functions of the two optical guides reverse. This produces an alternating image display at a speed that provides a perceived continuity of image. A video monitor with shielded filters synchronized with the light switching intervals displays the image.

U.S. Pat. No. 4,926,257 to Miyazaki also discloses a stereoscopic endoscope. A common light supply illuminates two sets of optical fibers that convey images from two separate objective lenses. The images are multiplexed into a electronic system for display through a filtered output that operates in synchronism with the switching of the optical paths.

In accordance with a third approach, an endoscope produces images for display on a virtual reality viewing device. For example, U.S. Pat. No. 4,651,201 to Schoolman discloses a stereoscopic endoscope. A sheath for insertion in the body of a patient contains a pair of image guides and an illumination light guide, preferably formed of optical fibers for flexibility. The image guides optically connect to a stereoscopic viewer for three-dimensional viewing of the site in the body. In one embodiment the viewer includes couplings for attaching miniaturized video cameras that are in turn connected to a stereoscopic video display mounted in headgear.

U.S. Pat. No. 5,647,838 to Bloomer discloses a holder that supports two monoscopic endoscopes in a distally convergent alignment to view an object along axes at a predetermined convergent angle. Video cameras attach to the proximal ends of each endoscope. A multiplexer then conveys the signals from the two cameras to the three-dimensional viewing devices. The glasses in such a viewing device provides an image which the individual perceives in three dimensions.

Apparatus incorporating the first approach of direct viewing are often cumbersome to use. The devices become physically large as they must have eyepieces conformed to align with an individual's eyes. Only direct viewing is available by the person handling the endoscope. There is no way to provide a remote image. Consequently for these and other reasons this approach has not gained wide favor within the medical community.

Stereoscopic endoscopic devices according to the second approach have also failed to gain wide-spread acceptance. The required electronics increases costs. Individuals using these devices during long medical procedures have reported some eye fatigue apparently produced by the images switching.

The third approach has produced more promise but as yet has not found any commercially acceptable embodiments. The structure in the Bloomer patent, for example, relies upon the holder to establish a divergent angle physically. Consequently the endoscopic structure widens as it extends proximally and can limit the distance by which the endoscope can enter a body without requiring an otherwise unnecessary large entry site. The Schoolman patent suggests an endoscope with parallel endoscope axes that would minimize the entry site. The disclosure seems to suggest attaching video cameras to each of the eyepieces thereby to reproduce what would otherwise be seen by direct viewing. Moreover, the Schoolman patent indicates a preference for a fiber optic image guide. Experience shows that the spatial and contrast resolutions provided by such fiber optic systems does not provide an image with sufficient definition for many applications.

SUMMARY

Therefore it is an object of this invention to provide a stereoscopic endoscope and related apparatus for enabling an individual to view an object within a body in three dimensions.

Another object of this invention is to provide a stereoscopic endoscope that produces three-dimensional images with high contrast and spatial resolution.

Still another object of this invention is to provide a stereoscopic endoscope that uses virtual reality viewing devices for producing an image that can be viewed with minimal eye fatigue.

In accordance with one aspect of this invention a stereoscopic endoscope comprises first and second endoscopes each of which has an objective lens at a proximal end and an image transfer mechanism for transferring an image along an image transfer axis to the proximal end of the endoscope. The first and second endoscopes are supported with their image transfer axes in a parallel relationship. First and second video devices at the proximal end convert optical images from each of the endoscopes into video signals. First and second folded optical paths, that each include one adjustable reflective surface, convey the images from the proximal ends of each endoscope to a corresponding one of the video devices. A virtual reality display device connects to the first and second video means for providing the stereoscopic view. This device includes first and second video monitors that connect to the first and second video devices. Each of the reflected surfaces are positioned to superimpose the images from the first and second video means thereby to provide the viewer with images that can be perceived in three dimensions.

In accordance with another aspect of this invention a stereoscopic endoscope system comprises an endoscope apparatus, a headset to be worn by an individual that includes first and second monitors and a video controller that connects the first and second monitors to the endoscope apparatus. The endoscope apparatus includes a housing at a proximal end and a tubular sheath that extends from the housing to the distal end. Illuminating light is conveyed from the proximal end through the housing and the tubular sheath to be projected from the distal end onto the object to be viewed. First and second endoscopes are carried in the tubular sheath along spaced parallel image transfer axes image the object along different optical axes extending from the distal ends thereof. A folded optical path supported in the housing transfers the images from the first and second endoscopes in a proximal direction. First and second video devices supported in the housing generate first and second video signals at the first and second outputs thereof in response to the images from said folded optical path. The monitors display the images to enable an individual to perceive a three-dimensional image of the object.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 2 is a top view of the apparatus in FIG. 1;

FIG. 3 is a layout view taken along lines 3—3 in FIG. 2;

DESCRIPTION OF ILLUSTRATIVE EMBODIMENTS

Figure 1:
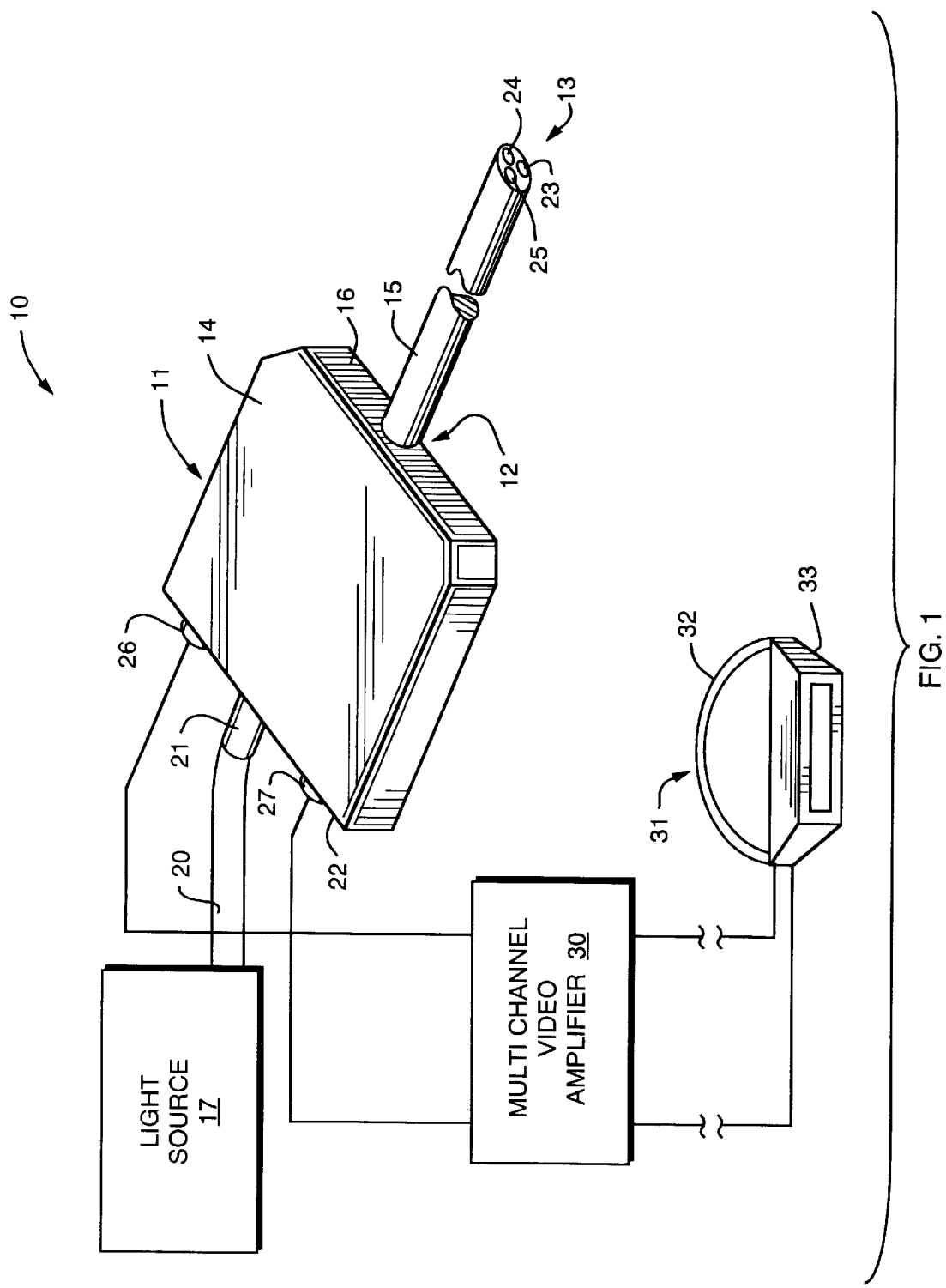
FIG. 1 is a view, partially in perspective and partially in schematic form of a stereoscopic endoscope system constructed in accordance with this invention.

A stereoscopic endoscope system 10 as disclosed in FIG. 1 comprises an endoscope apparatus 11 that extends from a proximal end 12 to a distal end 13. The endoscope apparatus 11 includes a housing 14 at the proximal end 12 and a tubular sheath 15 that extends from an end 16 of the housing 14 to the distal end 13. Light from an external light source 17 is conveyed through an optical fiber or other light conducting material 20 to a coupler 21 at a proximal end 22 of the housing 14. Light from the source 17 exits the sheath through a fiber optic port 23 at the distal end 13 and illuminates an object.

The tubular sheath 15 carries first and second endoscopes 24 and 25 shown at the distal end of the sheath 15. The sheath 15 carries the endoscopes 23 and 24 along spaced, parallel image transfer axes. As will become apparent, the housing 14 carries optical elements for defining two folded optical paths whereby images produced by each of the endoscopes 24 and 25 are conveyed to video cameras, the electrical outputs of which are designated by reference numerals 26 and 27. A multichannel video amplifier 30 receives the video outputs, processes them in a conventional manner for display on a virtual reality viewing device 31. The device 31 typically includes a headband 32 and a structure 33 that carries monitors that are located proximate an individual's eyes. They are typically called left and right monitors.

A surgeon utilizes the endoscopic device with its enlarged housing in a normal manner, the housing 14 remaining outside the patient, while wearing the headgear 31. As the distal end 13 moves through a passage, light from the source 17 illuminates any object within the field of view. The video cameras produce signals at the outputs 26 and 27 that are then conveyed to individual monitors so that any person wearing the headset perceives the image as a three-dimensional image.

Now referring to FIGS. 2 and 3, the apparatus is shown with portions of the housing 14 removed. The tubular sheath 15 carries the first and second endoscopes 24 and 25 along first and second endoscope axes 24a and 25a respectively. A fiber optic light pipe 35 extends from the coupler 21 through the housing 14 and through the sheath 15 to emerge from the distal end 13 at the port 23. Images from the endoscope 24 are conveyed from an objective lens 36 that is described in more detail later. An image transfer guide 37 produces an output of collimated light from proximal ends 40 of the endoscope 24. A similar objective lens (not shown) produces an image for the endoscope 25 that also includes a similar image transfer guide.

The construction of a preferred embodiment of the endoscopes 24 and 25 is disclosed later. However, for purposes of this discussion, it is sufficient to understand that the light from the proximal ends 40 and 41 each of the endoscopes 24 and 25 is collimated, or nearly collimated.

A folded optical path redirects this light from the endoscopes 24 and 25. More specifically, a stationary fold mirror 43 includes two 45° reflecting surfaces 44 and 45 that receive the light from the endoscopes 24 and 25 respectively. Light reflected from the surface 44 travels along a first axis that is 90° to the endoscope axis 24a and outwardly to an adjustable mirror 46 that reflects the light onto a offset axis 47 that is typically parallel to the endoscope axis 24a. Similarly the reflecting surface 45 reflects the image from the endoscope 25 onto an adjustable mirror 50 that redirects the light along an offset axis 51 that typically is parallel to the endoscope axis 25a and parallel to the offset axis 47. The distance between the axes 47 and 51 is set according to various physical constraints, typically the center line spacing of two video cameras 52 and 53.

Each of the video cameras has a conventional construction and includes a focusing lens, such as the focusing lenses 54 and 55, thereby to adjust the image size on the LCD or other similar light sensitive surface. The electrical power for and electrical signals from the first and second video cameras 52 and 53 are provided through connectors 56 and 57 that constitute the outputs 26 and 27 of FIG. 1, respectively. Thus the video signals at the connectors 56 and 57 represent outputs of the individual images formed by the endoscopes 24 and 25 respectively.

Figure 4:
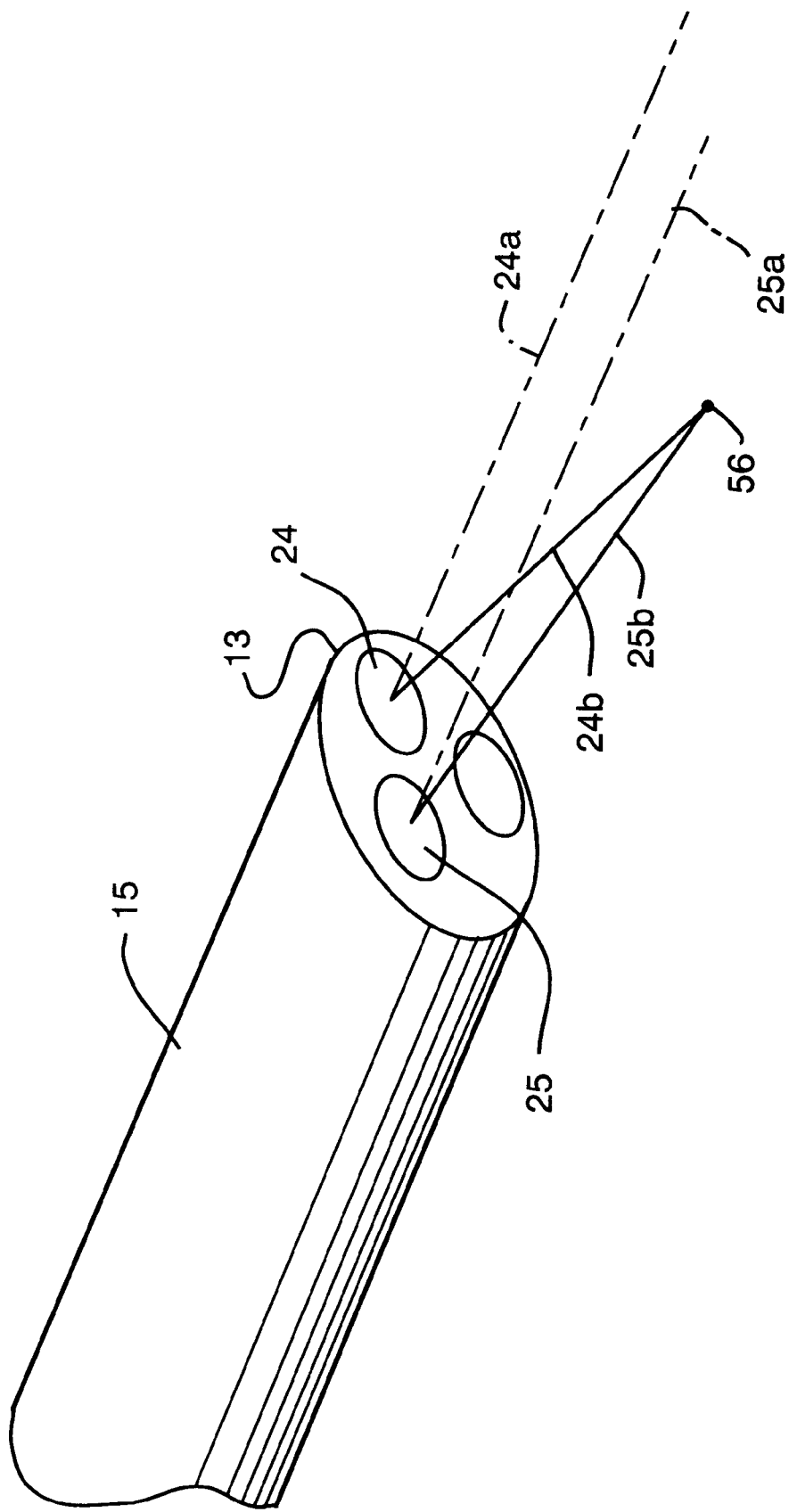
FIG. 4 is a perspective view for depicting the relationship between various axes in the apparatus of FIGS. 1 through 3.

FIG. 4 depicts a portion of the sheath 15 proximate the distal end 13 and particularly depicts the distal ends of the endoscopes 24 and 25 and respective endoscope axes 24a and 25a. Although an endoscope can be constructed to view an object lying in an endoscope plane defined by the axes 24a and 25a, a preferred version is to have a "side looking" endoscope view. That is, that the objective lens assembly 36 shown in FIG. 3 views an object along an optical axis 24b that is deflected some angle, $\alpha$, to its respective endoscope axis. Although this deflection can be in the range 0° to 90°, preferred embodiments incorporate deflection angles of $\alpha=30°$ and $\alpha=45°$.

In this device both endoscopes are constructed with the same deflection angle. Thus the endoscopes 24 and 25 image an object distally of the distal end 13 along optical axes 24b and 25b as shown in FIG. 4. Assuming that the endoscope optics are designed to image an object located at a position 56, the endoscopes 24 and 25 are rotated about their endoscope axes 24a and 25a such that their respective optical axes 24b and 25b intersect at the location 56. Thus the optical, or field of view, axes 24b and 25b, lie in a field of view plane that is oblique to the endoscope plane defined through the endoscope axes 24a and 25a. The use of such an oblique angle between the endoscope axes and the field of view axes does not effect the operation as previously described.

Figure 5:
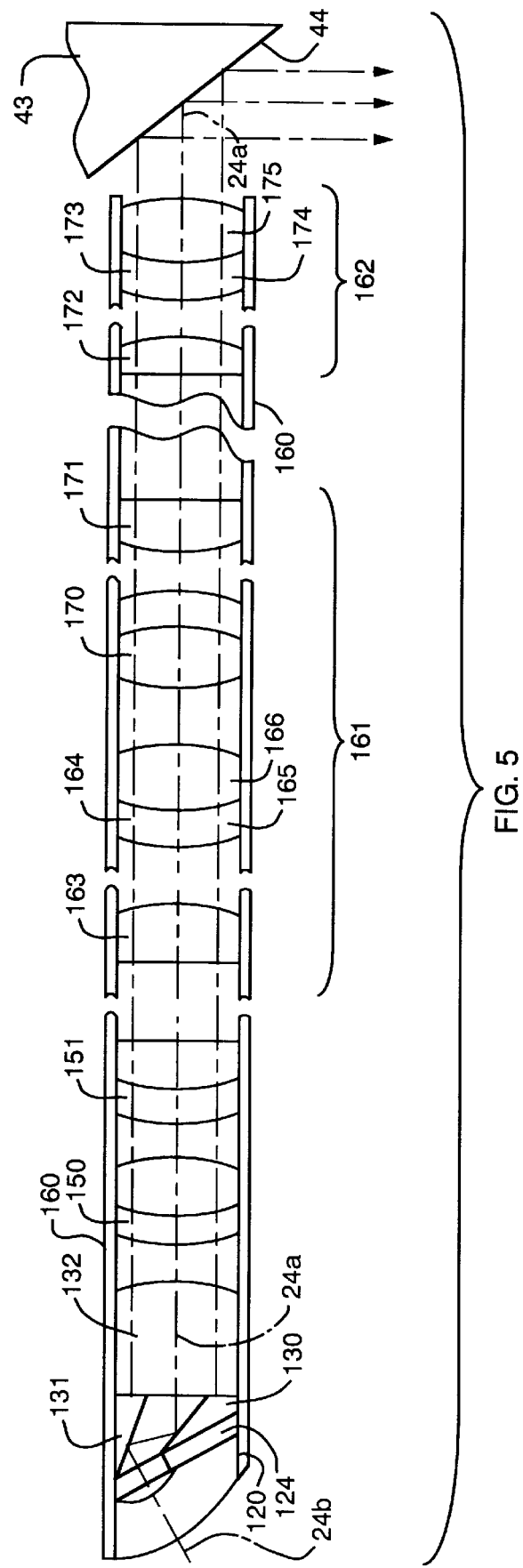
FIG. 5 is a diagram of a specific endoscope that is useful in apparatus incorporating this invention.

FIG. 5 depicts one embodiment of an endoscope that can be used as each of the endoscopes 24 and 25 in the apparatus of FIG. 1 to provide a stereoscopic image of high quality. As described in the above-identified U.S. patent application Ser. No. 08/883,216 the endoscope 24 includes a spherical objective lens 120 at the distal end 13 for producing an image of an object proximate the intersection of the field of view axes 24b with the corresponding axis from the other endoscope. The remaining elements of the objective lens system 120 include a shim 124, a prism including elements 126, 130 and 131, a plano convex lens 132 and doublets 150 and 151. All these elements are disclosed as lying in a sheath 160 that could be the inner surface of a lumen through the sheath 15 in FIG. 1 or a separate sheath to allow the pre-assembly of the endoscope 24 and insertion into the lumen 24. The latter approach is preferred because, as will become apparent, it is necessary to rotate the endoscope about the endoscope axis 24a to position the field of view axis 24b at the position 56 of the object.

The image transfer guide comprises a plurality of lens sets. A lens set 161 includes, from the distal to proximal ends, a piano convex lens 163, a doublet 164 including a concave convex lens 165 and a biconvex lens 166. A doublet 170 has the same construction as the doublet 164, but is reversed by 180°. A plano convex lens 171 is the last lens in the lens set 161. The total number of lens sets will depend primarily upon the length of the endoscope and the optical characteristics of a single lens set. Co-pending U.S. patent application Ser. No. 08/883,216 discloses a specific lens design that is appropriate for the objective lens 120, the lens set 161 and a final lens set 112.

In accordance with this invention the final lens set 162 comprises essentially one-half the lens set 161. That is the lens set 162 comprises a piano convex lens 172 and a doublet 173 including a concave convex lens 174 and a biconvex lens 175. When this particular embodiment of the biconvex lens 175 is at the most proximal position of the sheath 160. Proximally directed light rays from the doublet 173 are collimated, that is, they are parallel or nearly parallel to each other. The doublet 173 directs this collimated light toward the reflecting surface 44 formed by the mirror 43. Thereafter the parallel rays are reflected from the adjustable mirror 46 to the video camera 52. With this lens construction the image at the video camera has minimal distortion and other aberrations that are critical to the perception of a good three-dimensional image.

Figure 6:
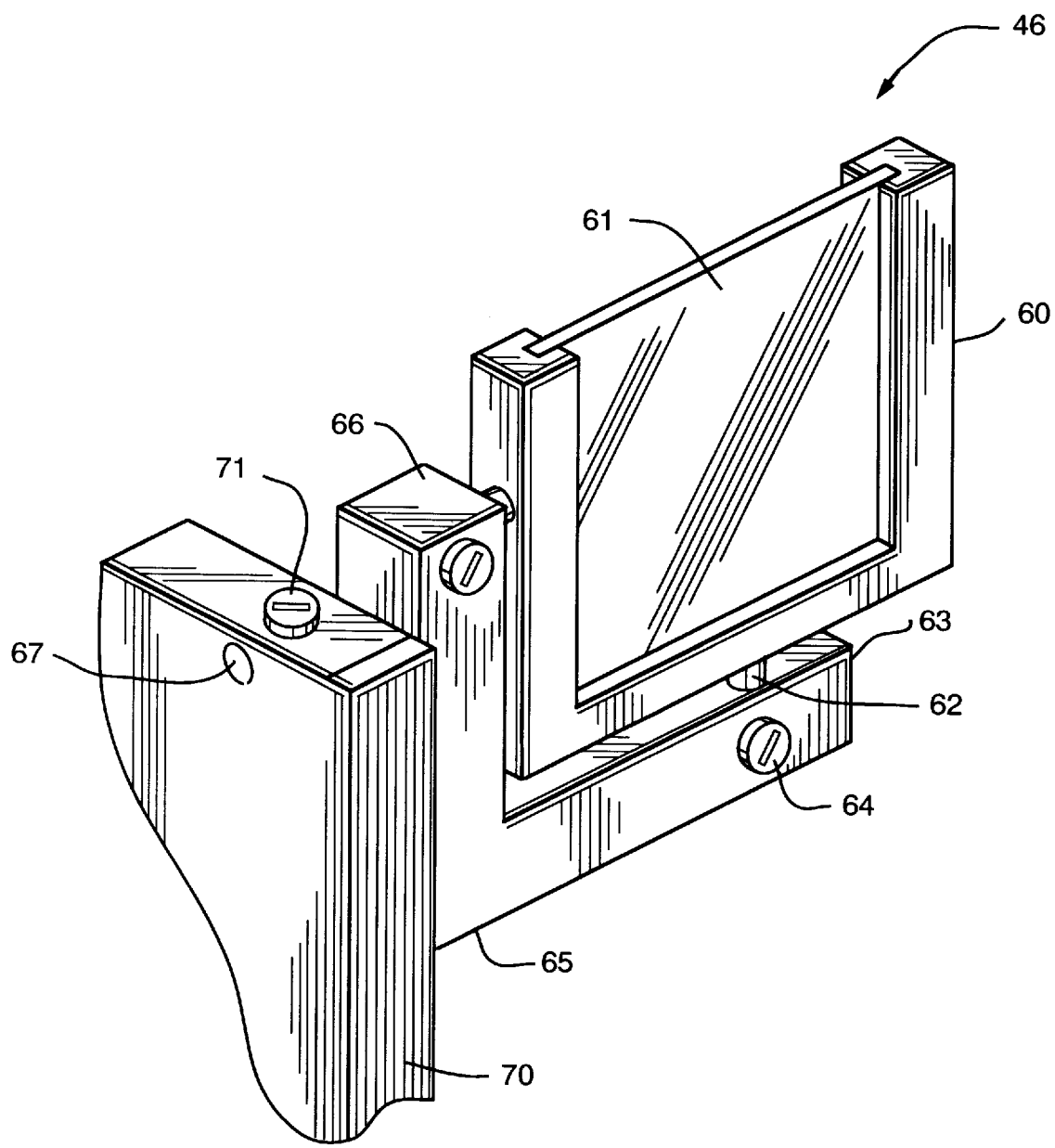
FIG. 6 is a perspective view of a mirror assembly that is shown conceptually and useful in apparatus incorporating this invention.
Figure 7:
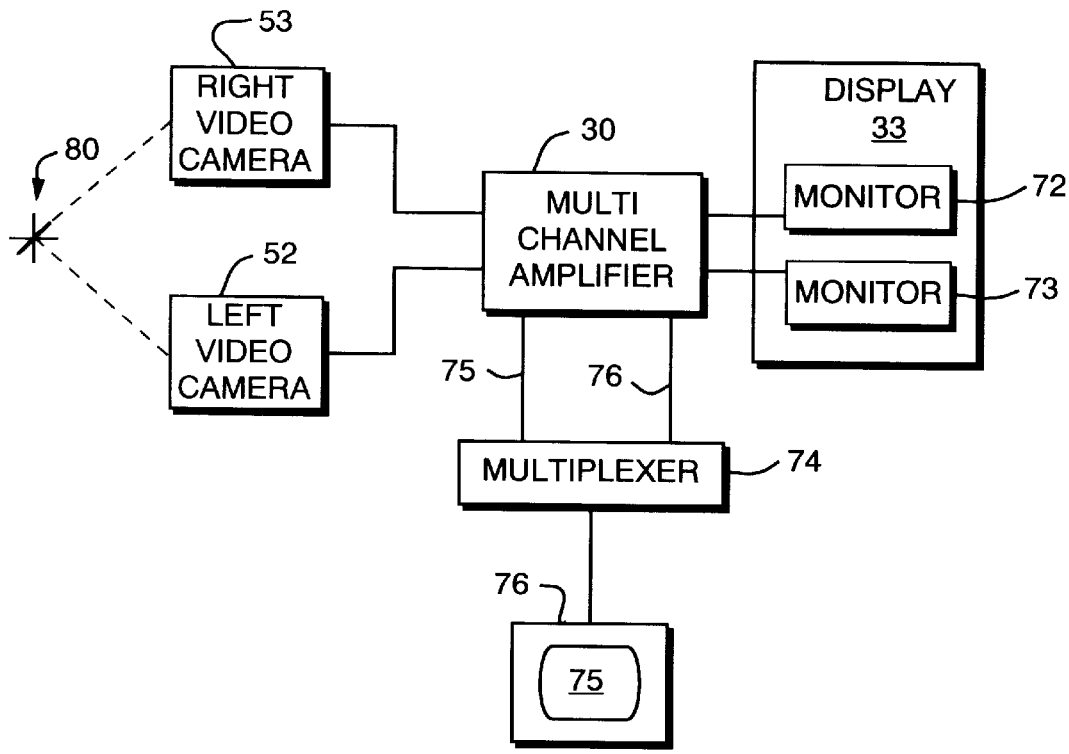
FIG. 7 is a schematic of a system for calibrating the endoscope system of FIG. 1.

The quality of the image provided to a surgeon is further enhanced by assuring the superposition or registration of the two images. FIGS. 6 and 7 depict representations of elements that assure this superposition. As previously indicated, the mirrors 46 and 50 are adjustable with two degrees of freedom. One particular structure, shown conceptually in FIG. 6, comprises a U shaped frame 60 that carries a reflecting mirror 61. The U shaped frame 60 has a vertical shaft 62 extending from the center line thereof into a horizontal support 63. This allows the frame 60 to rotate about a vertical axis. A set screw 64 or the like fixes the frame 60 in the horizontal support.

The horizontal support 63 is formed integrally as an element of an L shaped support 65 with a vertical arm 66. A shaft 67 affixed to the vertical arm 66 lies on a central horizontal axis of the mirror 61. Thus the support 65 can rotate about the horizontal axis when the shaft 67 rotates in a vertical support 70. A set screw 71 then locks the support 65 in an appropriate angle of rotation about the horizontal axis.

Referring to FIG. 7, the left and right video cameras 52 and 53 provide signals to a multichannel video amplifier 30 that then produces output signals for energizing miniaturized television monitors 72 and 73 carried by the monitor support 33. Multichannel amplifiers 30 such as shown in FIG. 7 often have multiple outputs. A multiplexer 74 can connect either to independent outputs 75 and 76 or can connect into the connectors 56 and 57 in FIG. 2 for an alignment procedure. The multiplexer 74 then displays the images from the left and right video cameras 52 and 53 "simultaneously" on a video screen 75 of a monitor 76.

Figure 8:
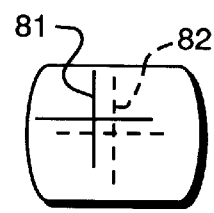
FIG. 8 shows misalignment of two target images.

If the mirrors are not aligned appropriately, an image of a target 80 may produce two target images 81 and 82 as shown in FIG. 8. Rotation of the mirrors about the horizontal and vertical axes by mechanisms such as shown in FIG. 6 bring the two targets into registration and center those targets on the screen.

Figure 9:
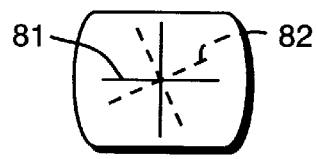
FIG. 9 shows angular misalignment of two target images.

FIG. 9 depicts an image produced when the target image 81 is centered on the screen and the target image 82 is centered on the screen but rotated with respect to the target image 81. Alignment is readily achieved by releasing one or the other of clamps 83 and 84 shown in FIGS. 2 and 3 to allow the video camera 52 or 53 producing the rotated target to be rotated physically thereby to bring the target 82 back into angular alignment.

These mechanisms, namely the mirror holding structure shown in FIG. 6 and the clamps in FIGS. 2 and 3, provide a means for simply bringing both the images into registration during the production phase when combined with the components shown in FIG. 7. Such a system is readily adapted for compensating any manufacturing tolerances that might otherwise exist in the product when such a product is mass produced.

In summary there has been disclosed a stereoscopic endoscope that utilizes headgear that is readily available as a virtual reality viewing device. The endoscope apparatus comprises two endoscopes that extend along parallel axes and optically view an image that lies on the convergence or proximate a convergence of field of view axes. Endoscopic devices normally are established to view at a particular site at a particular distance from the endoscope. Rotation of the individual endoscopes within the sheath facilitates this operation, particularly when combined with the previously described adjustment mechanisms for the mirrors and video cameras. Tests show that a stereoscopic endoscope constructed in accordance with this invention produces a high quality image that is readily perceived in three dimensions. The resulting image is bright and has high contrast. It is also characterized by the inherent high spatial resolution provided by glass lenses. As the image displayed on each monitor is continuous and as residual manufacturing misalignment has been removed, inherent eye fatigue problems observed in certain of the prior art devices are eliminated.

This invention has been disclosed in terms of certain embodiments. As will be apparent to those skilled in the art, different lens configurations can be substituted for the specifically disclosed objective lens and image transfer guide configurations. Different optical paths from the endoscopes to the video camera devices can be used. It will also be apparent that many other modifications can be made to the disclosed apparatus without departing from the invention. Therefore, it is the intent of the appended claims to cover all such variations and modifications as come within the true spirit and scope of this invention.

What is claimed as new and desired to be secured by letters patent of the United States is:

1. A stereoscopic endoscope system comprising:
   A) first and second endoscopes, each endoscope having an objective lens at the distal end thereof and means for transferring an image along an image transfer axis formed by said objective lens to the proximal end of said endoscope,
   B) means for supporting said first and second endoscopes with said image transfer axes in a parallel relationship,
   C) first and second video means at the proximal end of said first and second endoscopes, respectively, for converting optical images into video signals,
   D) first and second means forming folded optical paths having at least one adjustable reflective surface for conveying an image from the proximal end of each said endoscope to a corresponding one of said video means along corresponding video axes,
   E) virtual reality means connected to said first and second video means for providing a stereoscopic view of the image, said virtual reality means including first and second video monitors connected to said first and second video means, each of said monitors projecting an image from a respective one of said first and second video means, F) first means for positioning each of said reflective surfaces to superimpose the images produced by said first and second video means thereby to present two images in register that are perceived in three dimensions, and G) second means for rotating at least one of said video means about its video axis thereby to enable angular alignment of the superimposed images.

2. An endoscope as recited in claim 1 wherein said endoscope support means includes a tubular sheath having first and second lumens for said first and second endoscopes and a third lumen and wherein said endoscope additionally comprises a light transmission means carried in said third lumen for conveying light from a source at the proximal end to the object being imaged.

3. An endoscope as recited in claim 2 wherein each of said endoscopes includes:

i. image transfer means in said sheath intermediate said proximal and distal ends for optically transferring an image from the distal end to the proximal end, and ii. objective lens means including a plurality of optical components at said distal end having, as the most distal of said optical components, a spherical objective lens for forming an image of an object along an optical axis for transfer through said image transfer means.

4. An endoscope as recited in claim 3 wherein said objective lens means includes a plurality of lens elements intermediate said spherical objective lens and said image transfer means, certain of said lens elements directing the image along the image transfer axis.

5. An endoscope as recited in claim 4 wherein said image transfer means in each of said first and second endoscopes comprises at least one relay lens.

6. An endoscope as recited in claim 5 wherein the image transfer axes of said first and second endoscopes lie in an endoscope plane and each of said endoscopes is characterized by a field of view extending along a field-of-view axis, said field-of-view axes lying in a field-of-view plane that is oblique to the endoscope plane.

7. An endoscope as recited in claim 6 wherein said field-of-view plane intersects said endoscope plane at an angle that is greater than 0° and less than 90°.

8. An endoscope as recited in claim 6 wherein said field-of-view plane intersects said endoscope plane at an angle of approximately 30°.

9. An endoscope as recited in claim 6 wherein said field-of-view plane intersects said endoscope plane at an angle of approximately 45°.

10. An endoscope as recited in claim 1 wherein said virtual reality means includes a headset that supports said first and second monitors for stereoscopic viewing of the images displayed thereby.

11. An endoscope as recited in claim 10 wherein each of said folded optical paths includes means for redirecting the images from said image transfer means along first and second transverse axes and first and second mirrors for directing the images 90° from said redirecting means to said first and second video means.

12. A stereoscopic endoscope system for viewing an object comprising:

A) endoscope apparatus extending between proximal and distal ends, said endoscope apparatus including:

i. a housing at the proximal end, ii. a tubular sheath extending from one end of said housing to the distal end, iii. means extending through said housing and said tubular sheath for connection to an external light source at the proximal end for conveying light for projection from the distal end onto an object to be viewed, iv. first and second endoscopes carried in said tubular sheath along spaced, parallel image transfer axes for imaging the object along different optical axes extending from the distal ends thereof, said endoscopes being positioned about their respective transfer axes such that the optical axes extending from the distal ends thereof intersect at a location to be imaged, v. folded optical path means supported in said housing for transferring the images from the first and second endoscopes in a proximal direction, vi. first and second video means supported in said housing along video axes for generating first and second video signals at first and second outputs thereof in response to first and second images from said folded optical path means, said housing including a releasable clamping means for enabling at least one of said video means to be rotated about its video axis thereby to enable angular alignment of the images transferred from said folded optical path means, B) a headset to be worn by an individual including first and second monitors for displaying images individually in alignment with the individual's first and second eyes, and C) video controller means connecting said first and second monitors and said first and second outputs whereby the images displayed on said monitors enable an individual to perceive a three dimensional image of the object.

13. A system as recited in claim 12 wherein each of said first and second endoscopes comprises fixed lenses.

14. A system as recited in claim 13 wherein each of said first and second endoscopes comprises a multiple lens objective lens system at the distal end for imaging an object along an optical axis and at least one relay lens system for conveying the image from said objective lens system to said optical path means.

15. A system as recited in claim 14 wherein said folded optical path means includes first surfaces for reflecting the images from said first and second endoscopes, first and second mirrors for receiving the first and second images reflected from said first surfaces onto said first and second video means respectively.

16. A system as recited in claim 15 wherein said folded optical path means additionally includes means for adjusting each of said first and second mirrors about two axes for centering the images on said video means.

17. A system as recited in claim 12 wherein the image transfer axes of said first and second endoscopes lie in an endoscope plane and each of said endoscopes is characterized by a field of view extending along a field-of-view axis, said field-of-view axes lying in a field-of-view plane that is oblique to the endoscope plane.

18. A system as recited in claim 17 wherein said field-of-view plane intersects said endoscope plane at an angle that is greater than 0° and less than 90°.

19. A system as recited in claim 18 wherein said field-of-view plane intersects said endoscope plane at an angle of approximately 30°.

* * * * *